United States Patent [19]

Peters

[11] 4,299,228
[45] Nov. 10, 1981

[54] SAFETY DEVICE FOR USE WITH A CANNULA

[76] Inventor: Joseph L. Peters, 282 Ballards Lande, North Finchley, London N.12, England

[21] Appl. No.: 56,608

[22] Filed: Jul. 11, 1979

[51] Int. Cl.³ .............................................. A61M 25/00
[52] U.S. Cl. ................................ 128/348; 128/214 R; 128/772
[58] Field of Search .............. 128/348, 349 R, 350 R, 128/341, 343, 214 R, DIG. 9, 656–658, 772

[56] References Cited

U.S. PATENT DOCUMENTS

| | | | |
|---|---|---|---|
| 2,649,092 | 8/1953 | Wallace | 128/349 R |
| 3,119,392 | 1/1964 | Zeiss | 128/348 |
| 3,854,477 | 12/1974 | Smith | 128/348 |
| 3,924,633 | 12/1975 | Cook et al. | 128/349 R |
| 4,085,757 | 4/1978 | Pevsner | 128/348 |

Primary Examiner—Bradley Garris
Attorney, Agent, or Firm—Brisebois & Kruger

[57] ABSTRACT

A safety device for leading a cannula through a subcutaneous tunnel is made in two parts moulded from synthetic material and releasably screw threaded together for receiving between them a cannula head member and holding the head member securely without crushing. The front part has a rear projection for closing the head member against entry of air and has a long, tapering forward projection for drawing the device and cannula held thereby through a subcutaneous passage. Instead of the forward projection a rod, flexible tongue or piece of thread may be provided.

7 Claims, 7 Drawing Figures

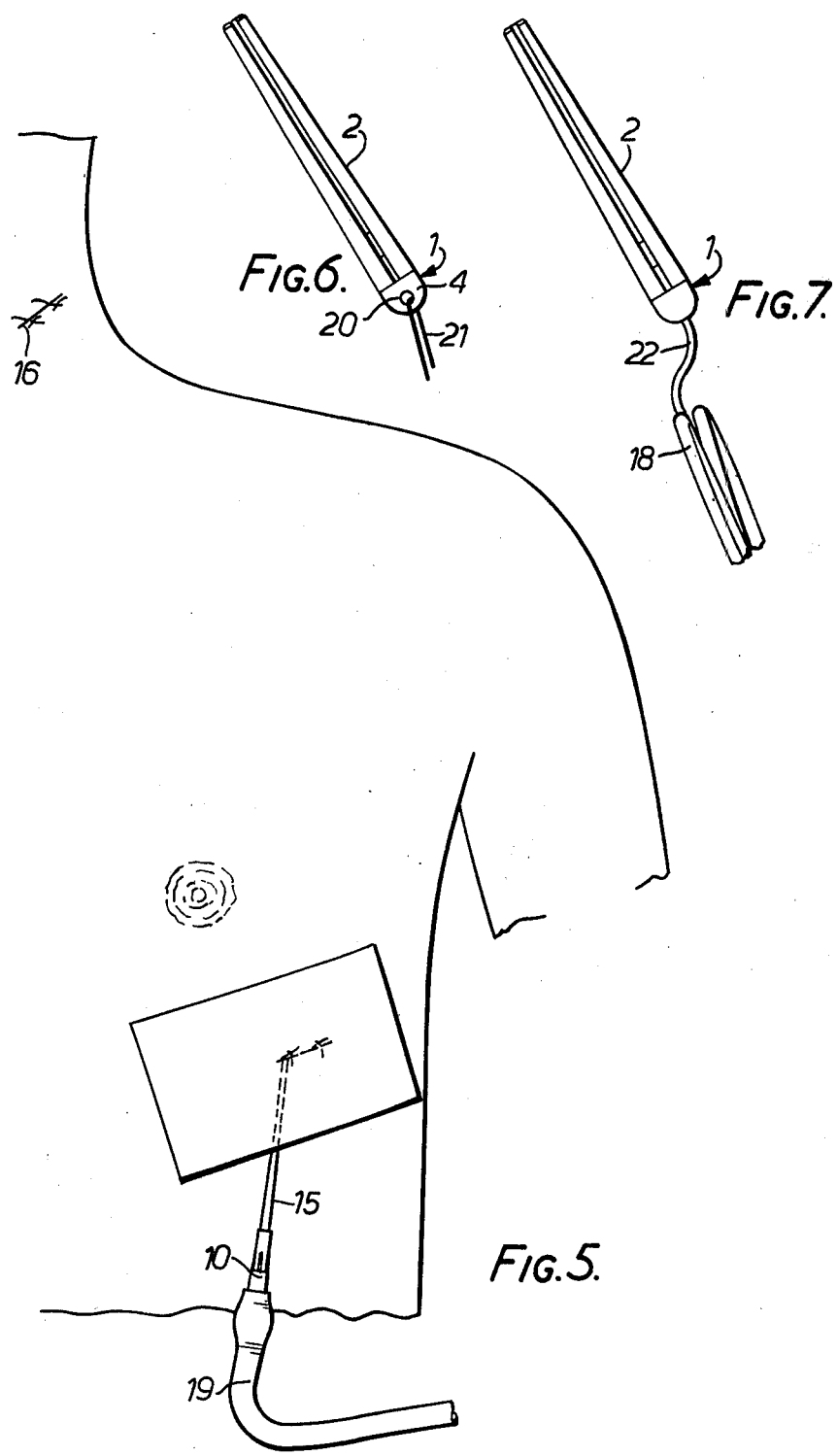

SAFETY DEVICE FOR USE WITH A CANNULA

When a hospital patient is fed intravenously it is usual for a cannula to be inserted into the internal jugular vein through the neck or the subclavian vein just behind the clavicle. In addition to the discomfort caused to a patient by the cannula emerging in the neck region it is difficult to maintain a clean wound at this part of the body. Perspiration around the neck tends to be comparatively high and there is a risk that bacteria will enter the wound and work their way along the cannula as a result of cannula motion caused by body movements of the patient. As the depth of the vein beneath the skin is small there is a danger that bacteria might enter the blood stream leading to septicemia, and this danger increases the longer the cannula is left in position.

To counter the risks involved with the above described techniques, for example when a patient is being given long term intravenous nutrition, it has been proposed to lead the cannula subcutaneously from the location where it enters the vein to a remote location, such as in the patient's chest, where the cannula emerges from the body. As a chest wound is easier to keep clean than one in the neck and the point at which the cannula leaves the body is comparatively remote from that where it enters the vein the dangers of septicemia are substantially reduced. The method of inserting the cannula as proposed requires the formation of a subcutaneous tunnel through which the cannula is pulled by gripping the cannula head member between the jaws of a pair of forceps. However cannulae head members are generally made of rigid plastics material and gripping them with forceps can fracture them. If a cannula head member becomes damaged, for instance cracked, during insertion and the damage goes unnoticed the consequences could be quite disastrous, as, for example, air embolism might result.

The present invention aims at a solution to the above problem and provides a safety device for leading a cannula through a subcutaneous passage, comprising means for receiving a cannula head member and adapted to hold the head member securely without crushing and with the tube of the cannula extending rearwardly from the device, and means at the forward end of the device for drawing the device and cannula held thereby through a subcutaneous passage, the forward end of the device having a smoothly tapering or rounded surface.

If the cannula is inserted into the vein of a patient it is of course essential that the open end of the head member be sealed against entry of air or foreign matter, and consequently the safety device will generally be employed in combination with or comprise means for sealing closed the end of the head member.

In accordance with one particular construction a safety device embodying the invention comprises two parts which can be screwed together to hold a cannula head member between them. The device has the general appearance of a capsule with a conically tapered or rounded nose which helps in passing the device through a subcutaneous passage. The cannula head member is received in an axial socket formed in a rear part of the device and a peg-like projection on the front part enters and seals the open end of the head member when the two parts of the device are screwed together.

Extending from the nose of the device is elongate, integral projection which is substantially rigid and can be used to pull the device through the subcutaneous tunnel. A rod fixed permanently to or detachable from the device can be used instead of the projection. Alternatively the device may have a loop of nylon thread or a flexible leader attached to the nose for drawing the device through the tunnel with a pair of forceps. The two parts of the device can conveniently be moulded from nylon or plastics material.

Some embodiments of the invention will now be described with reference to the accompanying drawings, in which:

FIGS. 3 to 5 show successive steps in the insertion of a cannula using the device of FIGS. 1 and 2;

FIGS. 6 and 7 show two alternative forms of safety device in accordance with the invention.

Figure 1:
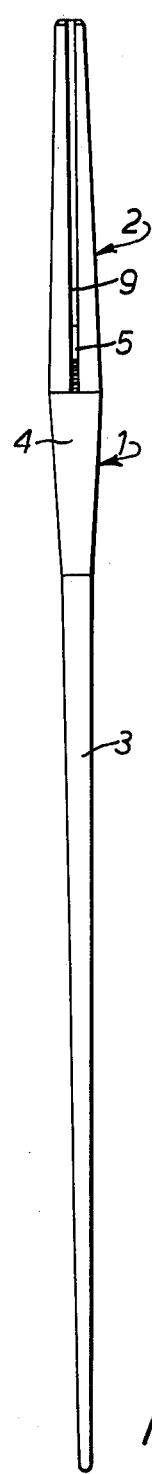
FIG. 1 is a side view of a safety device with the two parts thereof connected together.
Figure 2:
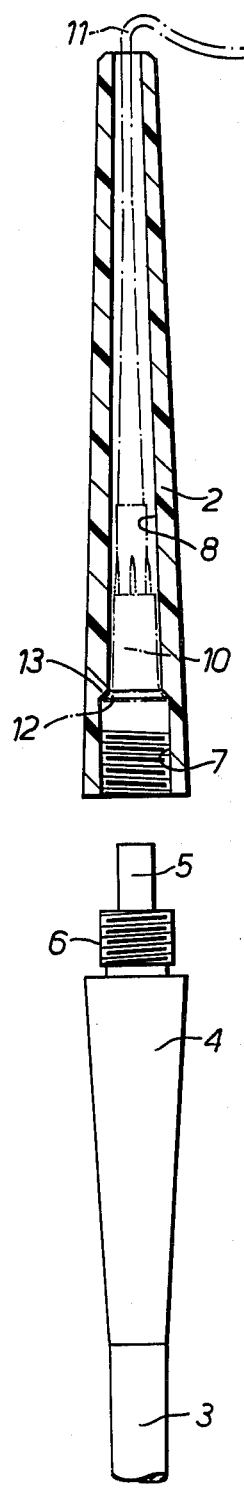
FIG. 2 is an axial cross-section of the device shown in FIG. 1 with the parts disconnected and shown on a larger scale.

The safety device illustrated in FIGS. 1 and 2 consists of two parts 1, 2 both moulded from synthetic plastics material. The first or front part 1 has a body portion 4 with an elongate forwardly extending projection 3 which tapers gradually towards its free end. A central rearwardly extending peg 5 on the part 1 has a very slight taper and is dimensioned for cooperation with a cannula head member. The part 1 is screw threaded at 6 for engagement with complementary screw threads 7 provided at the forward end of the second part 2 which is also formed with a stepped through bore 8 and a longitudinal slot 9 which extends the full length of part 2.

To attach the device to a cannula the parts are unscrewed and the peg 5 of part 1 is inserted into the open end of the cannula head member 10 to seal it closed. (The head member 10 is shown in FIG. 2 seated in the socket provided therefor in part 2). The part 2 is then located over the cannula tube 11 by inserting the tube through the slot 9 and the part 2 is moved along the cannula towards part 1. The two parts of the safety device are then screwed together so that the front end face of the part 2 abuts against the radial shoulder on the part 1 and a smooth external transition is formed between the parts 1,2. A flange or lugs 12 at the free end of head member 10 abut against an internal shoulder 13 of part 2 to prevent the head member being pulled off the peg 5 and out of the device.

Figure 3:
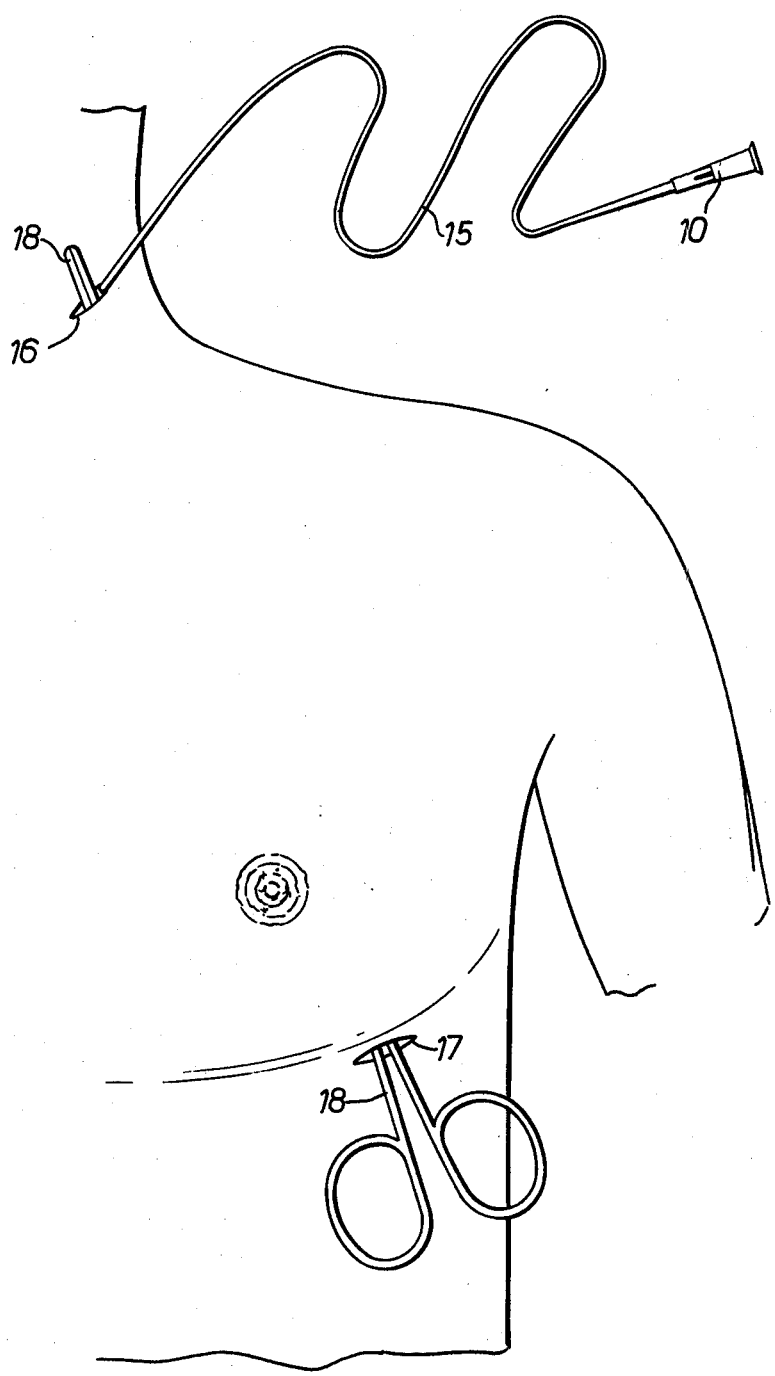
Figure 4:
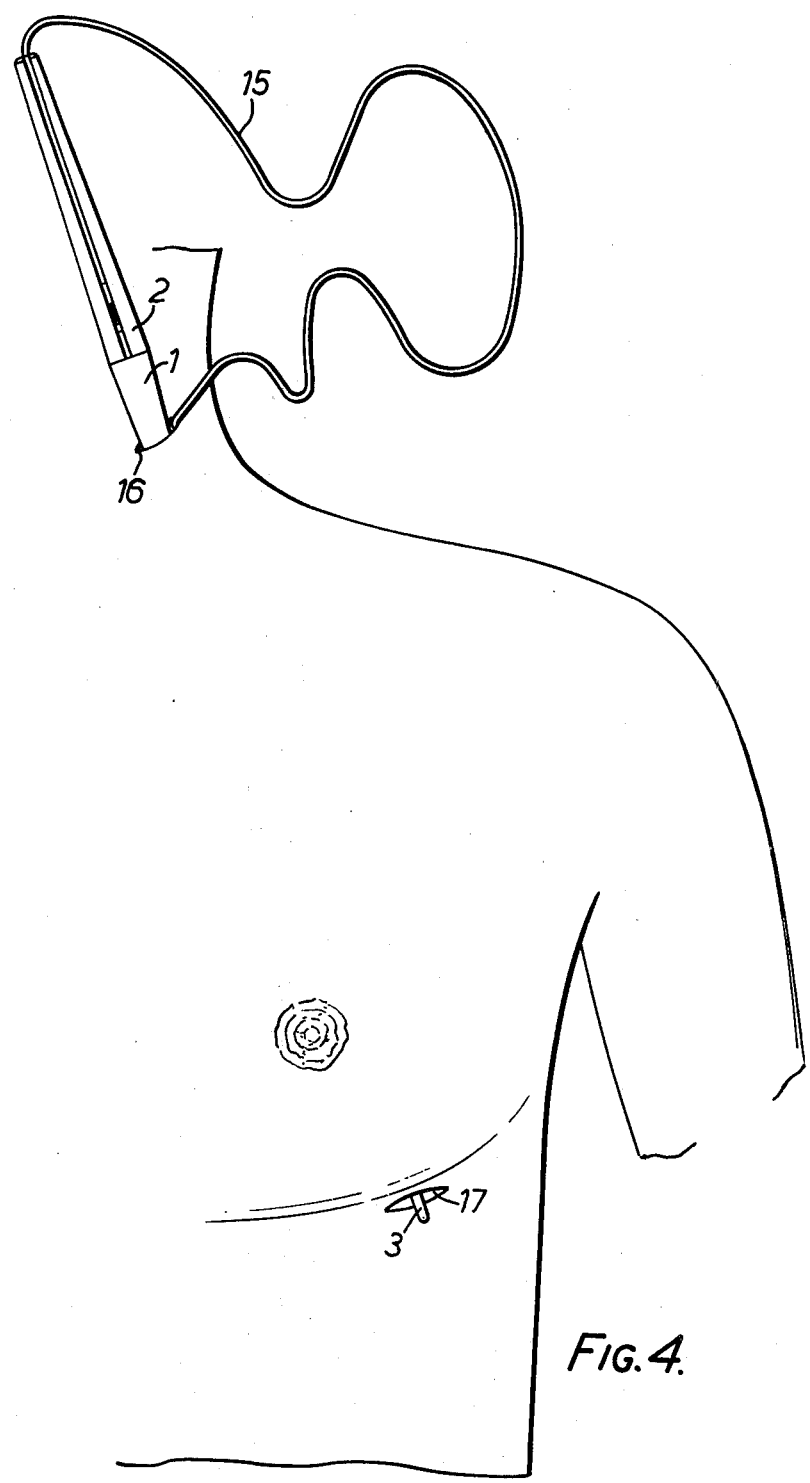

Use of the safety device will now be described with reference to FIGS. 3 to 5. The cannula 15 is inserted into the vein of a patient in the usual way by making an incision 16 in the neck. A second incision 17 is then made at a position remote from the first incision 16 and a pair of long forceps 18 is used to open up a subcutaneous tunnel joining the two incisions. The forceps are removed and the safety device is attached to the cannula 15 as described above. The device is then passed through the subcutaneous tunnel from the first incision to emerge through the second incision (FIG. 4), the tapered projection 3 acting as a leader or probe and the smooth outline of the device assisting passage of the device through the tunnel by preventing snagging. The safety device draws the cannula behind it and ensures that no excessive forces are exerted on the cannula head member. When the cannula has been drawn through the tunnel and no longer protrudes through the incision 16 the latter is stitched closed and the lower incision 17 through which the cannula emerges is dressed in the usual way (FIG. 5). The safety device is of course detached from the cannula which is connected to a giving set 19, for example.

It should be understood that the device may take many different forms without departing from the invention. Two modified forms of safety device are shown in FIGS. 6 and 7. The device of FIG. 6 differs to that described above in that the body 4 of the front part is hemispherical rather than conical and instead of the projection 3 the part 1 has a hole 20 in the body through which a loop 21 of nylon thread is passed. The device of FIG. 7 is similar but has a flexible tongue 22 integral with the body. With these two embodiments the nylon loop 21 or tongue 22 is gripped between the jaws of the forceps 18 used to open up the subcutaneous tunnel so that the device and cannula are pulled through the tunnel as the forceps are removed.

In another possible embodiment the device is similar to that of FIGS. 1 and 2, but instead of having the integral projection 3 the front part 1 is provided with an elongate rod, for example of metal, extending forwardly from the body 4 which tapers to the diameter of the rod, the rear end of the rod being moulded into the body 4.

It is not essential that the device itself should seal the end of the cannula and a sealing device known per se could be used for this purpose when the safety device is in use.

It is also possible to form the front part 1 of the device so that a nylon loop, flexible tongue or rigid rod can be selectively fixed thereto to suit the requirements of individual surgeons. Furthermore the device could be made in a single piece, for example one which screws onto or otherwise grips the head member of a cannula without exerting excessive forces thereon. It will also be appreciated that devices can readily be made for use with different makes of cannula. With the safety device shown in FIGS. 1 and 2 the part 2 can be configured internally to suit any particular type of cannula.

It is possible for the safety device of the invention to have a small hole through which a guide wire can be passed for guiding the device through a subcutaneous passage. For example the safety device shown in FIGS. 1 and 2 could have a hole passing from the top of the projection 3 to an opening in the threaded portion 6. In use the device would be slid along the guide previously threaded through the passage through which the cannula is to pass.

Other modifications and alternative forms for the safety device of the present invention will occur to those skilled in the art.

I claim:

1. A safety device for leading a cannula through a subcutaneous passage, the cannula having a tube and a head member attached to an end of the tube, the safety device comprising a front part and a rear part, said parts having complementary screw threads for threaded engagement and release of the parts, an axial bore in the rear part, a counterbore at the forward end of of said rear part for receiving the cannular head member and holding the head member securely without crushing and with the tube extending rearwardly through the bore, a longitudinal slot extending the full length of said rear part to allow the cannula tube to be inserted radially into said bore and then the head member to be moved axially into the counterbore, said front part being adapted to retain the head member in the counterbore when the front and rear parts are threaded together, and said front part including means for drawing the device and cannula held thereby through a subcutaneous passage and having a smoothly tapering or rounded surface.

2. A safety device according to claim 1, including closing means for sealing closed the head member to prevent air flowing into and through the tube of the cannula.

3. A safety device according to claim 2, wherein said closing means is integral with said front part of the device.

4. A safety device according to claim 3 wherein said closing means comprises a rearwardly directed projection on the front part of the device.

5. A safety device according to claim 1 wherein the drawing means on the front part comprises a substantially rigid elongate element.

6. A safety device according to claim 5 wherein said element comprises a projection formed integrally with said front part.

7. A safety device according to claim 5 wherein said element comprises a rod permanently or detachably connected to said front part.

* * * * *